(12) United States Patent
Greeven et al.

(10) Patent No.: US 6,832,200 B2
(45) Date of Patent: Dec. 14, 2004

(54) APPARATUS FOR CLOSED-LOOP PHARMACEUTICAL DELIVERY

(75) Inventors: John Greeven, Corvallis, OR (US); Michelle D. Greeven, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 197 days.

(21) Appl. No.: 09/949,049

(22) Filed: Sep. 7, 2001

(65) Prior Publication Data

US 2003/0050730 A1 Mar. 13, 2003

(51) Int. Cl.[7] ............................................. G06F 17/60
(52) U.S. Cl. ................................ 705/3; 604/65; 604/66; 604/67
(58) Field of Search ............................ 705/3; 700/240, 700/244; 604/65, 66, 67; 607/60

(56) References Cited

U.S. PATENT DOCUMENTS

| | | | | |
|---|---|---|---|---|
| 5,558,640 A | * | 9/1996 | Pfeiler et al. | 604/67 |
| 5,653,681 A | * | 8/1997 | Ellingboe | 604/4.01 |
| 5,713,856 A | * | 2/1998 | Eggers et al. | 604/65 |
| 5,840,026 A | * | 11/1998 | Uber et al. | 600/431 |
| 5,865,744 A | * | 2/1999 | Lemelson | 600/407 |
| 5,957,885 A | * | 9/1999 | Bollish et al. | 604/67 |
| 6,053,887 A | * | 4/2000 | Levitas et al. | 604/500 |
| 6,070,761 A | * | 6/2000 | Bloom et al. | 222/81 |
| 6,164,920 A | * | 12/2000 | Nazarian et al. | 417/4 |
| 6,186,977 B1 | * | 2/2001 | Andrews et al. | 604/67 |
| 6,475,180 B2 | * | 11/2002 | Peterson et al. | 604/65 |
| 6,503,221 B1 | * | 1/2003 | Briggs et al. | 604/67 |
| 6,519,569 B1 | * | 2/2003 | White et al. | 705/3 |
| 6,558,346 B1 | * | 5/2003 | Yoshioka et al. | 604/67 |
| 6,562,001 B2 | * | 5/2003 | Lebel et al. | 604/65 |

* cited by examiner

Primary Examiner—Khoi H. Tran (57) ABSTRACT

A method of dispensing a pharmaceutical senses electrical signal representative of a physical condition of a patient and dispenses a therapeutic drug to the patient from a drug delivery appliance in response to either the electrical signal or a second signal from a health care provider.

20 Claims, 5 Drawing Sheets

APPARATUS FOR CLOSED-LOOP PHARMACEUTICAL DELIVERY

FIELD OF THE INVENTION

This invention relates to medical devices. In particular, this invention relates to medical devices that are used to dispense maintenance pharmaceutical drugs.

BACKGROUND OF THE INVENTION

Many individuals suffer from chronic health problems, such as asthma, epilepsy, cancer, diabetes and allergies, the treatment of which typically requires the regular delivery of precise amounts of medication for the patient's survival. Optimum treatment of such chronic illnesses frequently requires that therapeutic drug dosing to a patient change in response to certain patient conditions. Unlike the human body's ability to regulate itself, most medical treatments are administered somewhat "open-loop." In other words, there is no continuous and immediate sensing of the effect of a dosage by which subsequent dosages are changed.

Many present-day chronic illness treatment regimens can be modeled as open loop systems, i.e., there is no automatic modification or adjustment of a treatment regimen in response to changing patient conditions. Individuals with chronic and expensive-to-treat illnesses might live better and filler lives if other drug delivery regimens were available.

DETAILED DESCRIPTION OF THE PREFERRED EMBODIMENT

Figure 1:
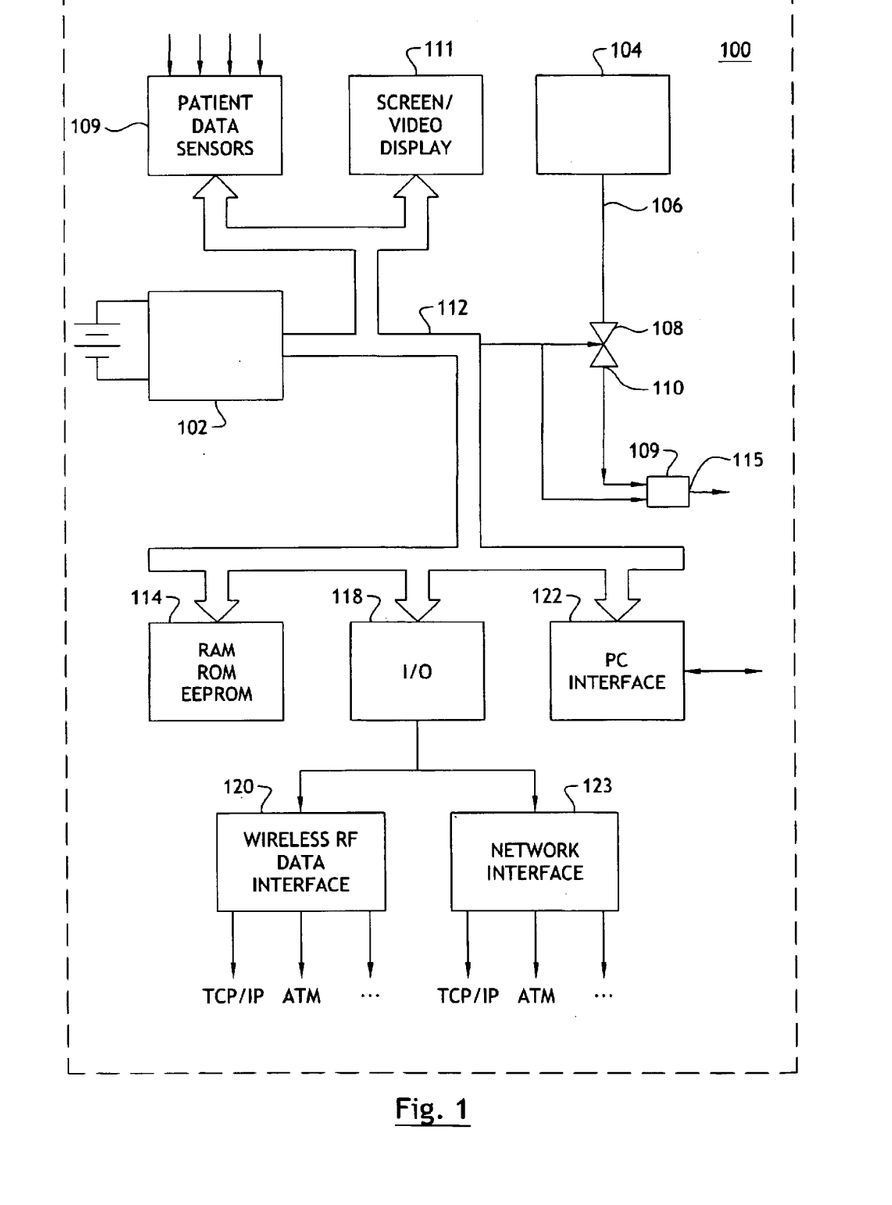
FIG. 1 shows a simplified block diagram of an intelligent drug delivery appliance.

FIG. 1 shows a simplified block diagram of an intelligent drug delivery appliance 100 (hereafter the "appliance"). The appliance 100 includes a controlling processor 102 (e.g., a microcontroller, microprocessor, digital signal processor (DSP), combinational/sequential logic and equivalents thereof), operatively coupled to peripheral devices (via an address/data/control bus 112) which include, but which are not limited to, a pharmaceutical control or dispensing valve or gate 108 of a reservoir 104 of a pharmaceutical (e.g. a drug or supply such as a hypodermic needle and syringe). The appliance 100 might be implanted into a patient but it might also be used as an in vitro device in a patient's home, hospital room or other location whereat treatment is administered or received.

The reservoir 104 can contain one or more supplies of controlled or medicinal substances such as tablets, liquids, gases, intended to be administered to a patient according to a treatment regimen (i.e. a prescription) of a medical professional (i.e. a doctor, not shown). The reservoir 104 might also store dispensable supplies, such as syringes, reagent test strips (for blood glucose testing for example) antihistamine tablets and the like, also to be used according to some prescribed treatment regiment. For purposes of claim construction, any substance or consumable supply item that might be dispensed to, or used by, a patient is hereafter referred to as a "pharmaceutical."

One specific example of a pharmaceutical, which might be controllably dispensed, is an aerosol or atomized mist of liquid anti-histamine. By using ink-jet print head technology, very precise amounts of liquids can be controllably dispensed under software control. As the amount of medication is used, the amount remaining in a reservoir can be readily determined.

In a drug delivery appliance such as that shown in FIG. 1, a treatment "regimen" (which is a schedule or circumstance according to which a pharmaceutical is taken by, or administered to a patient from the drug delivery appliance 100) is embodied as computer program instructions (and/or data) stored in a memory device 114 such as random access memory (RAM), electrically erasable programmable read only memory (EEPROM) or the like, within the appliance. Data parameters that the program operates on, or under the control of, are also stored in a memory device 114. By executing stored program instructions, the controller 102 can reliably administer pharmaceuticals according to a doctor's treatment regimen, the parameters of which can be changed by changing various data stored in memory 114.

By way of example, the program stored in ROM/EEPROM memory 114 (or possibly stored within memory of the processor 102 itself) can effectuate the administration of the aforementioned antihistamine (an example of a "pharmaceutical") from the reservoir 104 to a patient over a predetermined time interval (e.g., hourly, daily, weekly) or, for emergencies, upon patient demand, by opening a valve or gate or other dispensing mechanism 108 for a predetermined amount of time so that a certain amount of the pharmaceutical can be delivered (e.g. flow) from the reservoir 104 to a patient through the valve, (or gate or dispensing mechanism) 108. A drug regimen can also limit the amount of medicine dispensed to a patient according to amounts previously dispensed over time. In such instances, overdoses can be avoided or eliminated by software or program dosage limits stored in memory.

Many drugs affect measurable conditions of a person's body. If a prescribed drug is known to affect one or more measurable characteristics such as temperature, heart rate, blood pressure or other characteristics, actively monitoring the characteristic(s) and modulating a drug therapy in real time can yield better patient care.

In a preferred embodiment, patient condition sensors 109 (one shown in FIG. 1) detect measurable characteristics (quantities) such as heart rate, blood pressure, blood sugar, temperature, electrocardiogram, encephalograph signals and waveforms are operatively coupled to the processor so as to provide real-time data signals that are representative of a patient's physical condition. For purposes of claim construction however, the data signals from patient condition sensors that are "representative of a patient's physical condition" should not be construed to include manually controlled electrical signals, such as those generated by a manually-operable switch closure in prior art devices, such as on-demand morphine delivery pumps and patient-operable pushbutton switches by which drug administration is controlled or controllable using the manual switch closure. The term "signals representative of a patient's physical condition" should be considered to refer to electrical signals (digital or analog) that are generated by electronic circuitry in response to or monitoring autonomic physical conditions such as temperature, heart rate, blood pressure, brain wave activity, blood sugar and the like.

In addition to patient conditions, in another embodiment, information or data about atmospheric or environmental conditions, which can affect a patient's health or well being, are also considered to be signals representative of a patient's physical condition. Examples of the information representative a patient's (actual, expected or anticipated) condition would include information on barometric pressure or pressure changes, allergen counts if such allergens might adversely affect the patient's health Environmental conditions such as ozone levels, humidity, ambient temperature, ultraviolet (UV) levels, pollen counts, mold spore counts and the like (for geographic regions) all of which are readily available from third parties, such as the National Weather Service.

By way of example, knowing or anticipating that ozone, UV levels or allergen counts are high, low, likely to increase or likely to decrease would enable drug dosage for afflictions to be adjusted before the actual increase or decrease occurred thereby providing for better patient care. In such an embodiment, the administration of one or more therapeutic medicines from the reservoir 104 by the processor 102 can then be modulated under software control in response to the information fed back by sensors 109 so as to provide optimal control of a patient's health. Environmental conditions or predicted changes can be obtained by the appliance 100 by way of web-hosted communications between the appliance and the web site of a data provider through the appliance's data communication port(s) 120, 123. E-mail or FTP file transfers also provide a mechanism by which health-affecting data can be obtained by the appliance in real time.

Patient treatment regimens that are executed by the processor within the appliance 100 and stored in the appliance 100 memory 114 can also be monitored or modified under the external control of a health care provider (not shown). Sensed data parameters, (such as temperature, heart rate and brain wave activity, etc., read from external sensors) can be forwarded to a health care service provider by the appliance 100 using well-known data transfers accomplished via either the wireless data interface 120 or a wireline data network interface 123. In one embodiment, the appliance can log onto a health care service provider's web site and send data to the web server for the patient's doctor or nurse. Still other embodiments permit the appliance to log onto a health care service provider web site and download treatment regimen modifications.

When real-time patient data read by the intelligent drug delivery appliance is forwarded to a health care provider, a treatment regimen stored in the appliance 100 can be adjusted in real-time, in response thereto, such as by the aforementioned web download, an FTP file transfer or even instructions telephoned to the appliance 100 user. Drug dosage limits, drug administration timing and/or frequency and the like, which parameters are stored in EEPROM or RAM, can be modified in response to patient conditions on a real time basis. By way of example, a patient's dosage of pain medication can be adjusted by sensed-conditions such as brain wave activity, heart rate, temperature as well as data on atmospheric conditions such as pollen count. Data and instructions (e.g. to modify a drug dosage) can be transferred to the appliance 100 using web-based (Internet) communication. Data can also be transferred from the appliance also be way of web-based data transfers.

Figure 3:
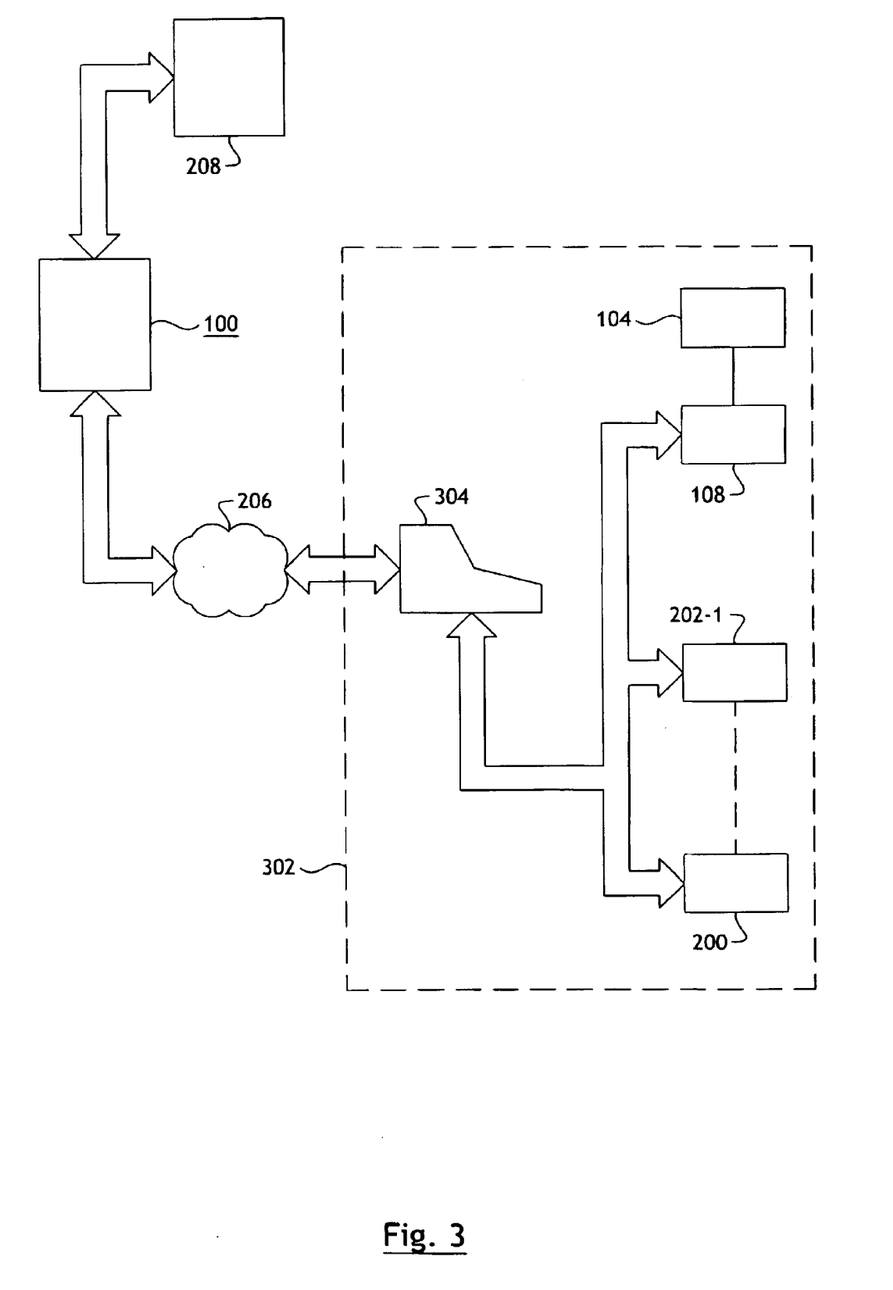
FIG. 3 shows an alternate embodiment of a networked drug delivery appliance.

In some embodiments, the drug delivery appliance 100 might be remotely located from the patient under treatment while the medication and dosage equipment remains proximate to the patient. FIG. 3 shows a simplified block diagram of an alternate embodiment wherein the drug delivery appliance 100 is remotely located from the patient-located equipment 302 but the drug delivery appliance 100 communicates with the patient located equipment via any appropriate data communications medium.

In FIG. 3, the intelligent drug delivery appliance 100 can be located in a health care service provider's office or at a nurses station for example but operatively coupled to patient sensors 202 by a data link 206. Inasmuch as the data link requires data it transfers to be in some particular format (e.g. TCP/IP, Ethernet, ATM, etc.) a personal computer 304 or other mechanism for coupling the data network (such as the Internet) to the patient is necessary. In the embodiment shown in FIG. 3, the computer 304 acts to convert data to and from the network so as to enable data communications between the remotely located appliance 100 and equipment located with the patient. By way of the terminal capabilities provided by the computer 304, the intelligent drug delivery appliance 100 can send and receive data to and from the remotely located sensors 202. The appliance 100 can also remotely control the delivery of pharmaceutical from the reservoir 104 by activating the delivery mechanism.

As shown in FIG. 3, sensors such as atmospheric condition sensors 208 (pollen, U.F., mold, etc.) can be co-located at the drug delivery appliance 100. As shown in FIG. 3, atmospheric sensors 208 can also be co-located with the patient equipment whereby patient atmospheric conditions can be determined enabling local atmospheric conditions to be monitored. In either case, signals (such as patient parameters or local atmospheric conditions) sent over a data network 208 are processed by the appliance 100 to render a pharmaceutical dosage. Once a dosage is determined, the appliance's responsive signal can be carried over the network 206 to the patient-located dispensing equipment 108, 104. By locating sensors 208 at the remotely located drug delivery appliance 100, expensive atmospheric monitoring equipment can be used without having to co-locate such equipment at several patient locations, data obtained by the sensors can be used to adjust medication dosages by signals sent to the dispensing equipment 104, 108 by way of data messages exchanged across the network 206. For purposes of claim construction, the remote processing by the appliance 100 is considered to be equivalent to the local processing using the embodiment shown in FIG. 2.

With respect to FIG. 1, a human/display interface 111 is operatively coupled to the processor 102 via the address/control and data bus 112. Real-time status information (on patient vital signs as well as pharmaceutical availability information or the detection of an operational failure of the drug dispensing appliance) can be displayed to an operator on the human/display interface 111, which could be embodied as a screen such as a CRT or LCD, which for simplicity are generically considered to be the human/display interface 111. Appliance status information (battery status; time of day; diagnostic status) can also be displayed under software control by the processor 102.

As part of the human/display interface, a keyboard or other tactile input device or speech recognition device can be used to input queries to the processor, such as a request to run diagnostic software or to display the amount of pharmaceutical that remains in the reservoir. A keyboard or other input device (e.g., push-button, softkey) can also be used to modify pharmaceutical dosing, providing for example, the capability of delivering an on-demand bolus of pharmaceutical, such as for allergy treatment.

For the visually-impaired, a speech synthesizer (not shown) can be employed to enunciate statistics and other information that would otherwise be displayed. Well-known speech recognition techniques (requiring a microphone input, audio processing and a data base (not shown) of recognizable words, all of which are well known) can be used in place of tactile/switch input devices.

Information, such as the volume of pharmaceutical remaining can be critically important to maintaining patient care. A patient-appropriate warning can be made so as to prevent unexpected depletion of a therapeutic. An audible alarm, flashing light or a combination thereof can be employed to alert an appliance 100 user. For purposes of claim construction, all of the foregoing implementations of a human interface are considered to be equivalent "human interface devices."

Figure 2:
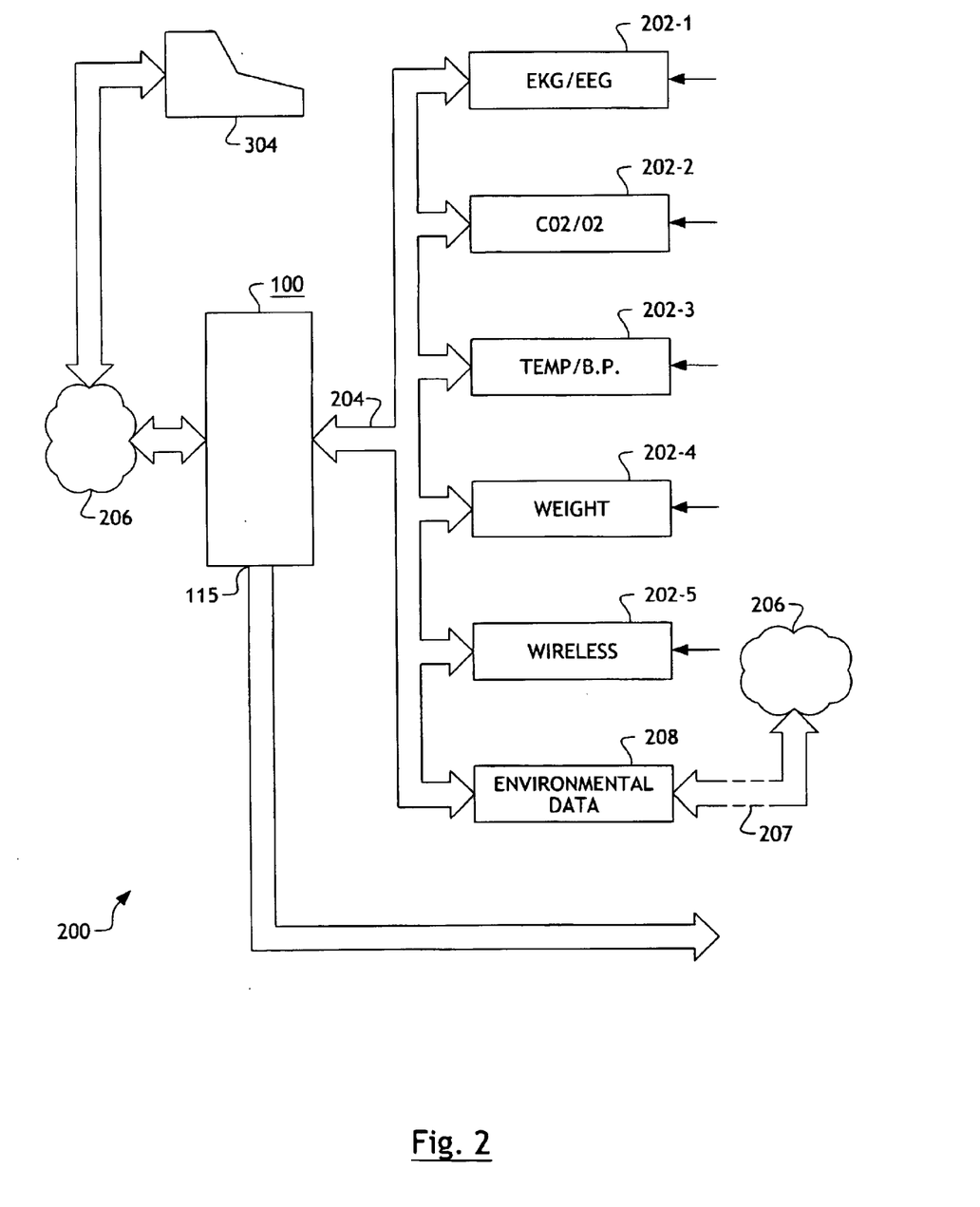
FIG. 2 shows a simplified representation of an intelligent drug delivery appliance and external sensors and a data network interface.

FIG. 2 shows a simplified block diagram of a closed-loop intelligent drug delivery system 200. An intelligent drug delivery appliance 100 (such as that shown in FIG. 1) includes a control/communications bus 204 over which signals between patient parameter sensors 202 (202-1–202-6) and a drug delivery appliance 100 are exchanged (bi-directionally) or carried (uni-directionally). Those skilled in the art will recognize that the bus 204 could be implemented using different techniques. For instance, a microprocessor's address, data and control lines could be used to read data from and write data to the sensors 202. Well-known control busses, such as a "USB" (Universal Serial Bus) RS 232, SCSI or HPIB (Hewlett-Packard Interface Bus) are but a few examples of other protocols by which data could be sent to and/or received from sensors 202.

The sensors 202 shown in FIG. 2 by simplified diagrammatic representations include an electrocardiogram (EKG/EEG) sensor 202-1. As is known by those skilled in the medical arts, an EKG includes waveforms that model or represent cardiac rhythm. EKG waveform anomalies can indicate a variety of cardiac problems, many of which are very responsive to drug therapy which can be administered by the appliance 100.

EKG waveforms are time-varying signals that are obtainable using electrodes attached to the patient. Signals from the electrodes (not shown) would represent raw data that requires appropriate processing by the appliance 100 (or another processor) such that the time-varying EKG waveforms can be analyzed to detect normal or abnormal waveforms.

An electroencephalograph (EEG) 202-1 can be useful to detect brain wave activity. EEG waveform abnormalities can indicate impending or existing illnesses or stroke for example. EEG waveforms (after processing) can be used to modulate the administration of certain therapeutics.

Blood gas analyzers (e.g., $O_2$,; $CO_2$) 202-2 can be used to adjust the delivery of respiratory therapy or supplemental oxygen. A patient's temperature and/or blood pressure can be read using a variety of techniques 202-3 and, in response thereto, a variety of regulatory medications be administered. Blood sugar sensors (not shown) or weight sensors 202-4 can also be used to monitor a patient and in response to conditions they detect, provide real-time upon which drug therapies can be adjusted in response to signals sent to drug delivery mechanisms (not shown in FIG. 2) via a control bus 115.

As set forth above in the discussion of FIG. 1, in addition to sensing a patient's vital signs and statistics, information on physical conditions or stimuli that might affect a patient's health can be obtained from extrinsic sources can be provided to the drug delivery appliance 100. Data or information on physical conditions that might affect a patient's health can include (but are not be limited to) atmospheric levels of certain pollutants or irritants such as ozone, humidity, ambient temperature and ultraviolet light. Actual and/or expected atmospheric levels of certain allergens such as pollen, mold spores, rag weed and the like, can also be sent to or read by the appliance 100. Information regarding ambient conditions might also be read by the appliance 100 directly from co-located sensors (not shown). For purposes of claim construction, information or stimuli that might affect a patient's health includes, but is not limited to: ambient temperature or humidity; ozone; ultraviolet light intensity levels; allergen counts and the like, and are all considered to be "environmental data." Such data (or information) is received by an environmental data collections interface 208 from either real-time sensors or third party data providers.

Environmental data can be provided to the drug delivery appliance 100 through the environmental data collection interface 208 by way of third-party service providers (not shown) such as the National Weather Service. Mold spore and pollen counts are regularly available from third parties via web sites on the Internet. Data on allergens and other environmental data can be sent to and/or received by way of a data network 206 (such as the Internet) to an environmental data collection interface 208. (The environmental data collection interface 208 can also include environmental data sensors which directly collect environmental data on their own. Examples of such sensors would include thermometers, UV light meters and the like.)

Environmental data transfers (data transfers of environmental data such as pollen counts, humidity, temperature, etc.) can be accomplished using data transfers, such as those descried in the currently co-pending patent application for a "METHOD AND APPARATUS FOR DELIVERING AND REFILLING PHARMACEUTICALS" which was filed on Mar. 29, 2001, assigned to the Hewlett-Packard Company, having U.S. patent application Ser. No. 09/823,188, the teaching of which is incorporated by reference as it relates to Internet data transfers between an intelligent drug delivery appliance and a third party service provider.

In a preferred embodiment, environmental data is readily obtained from third parties using a variety of data transfer schemes. Web servers of meteorological data providers for example might provide such data to the appliance 100 (or make it available for download) if the appliance has access to the Internet 206 via a data link 207. Using the logical addresses (URLs) of such web servers, environmental data can be requested and received by the appliance 100 for use in calculating an appropriate dosage of pharmaceutical.

When physically-measurable parameters of a patient's condition, (including environmental data) are read in "real time" (i.e. substantially instantaneously) by the appliance 100, close patient control can be improved by immediately adjusting drug dosages. Drug dosages can be reduced if symptoms abate or are expected to abate, saving the patient unnecessary dosing and saving the patient unnecessary cost. Conversely, drug dosages can be increased, if for example, pollen counts are predicted to rise wherever it is that the patient live.

For patients who take two or more different medications, adverse drug interactions can be avoided using the drug delivery appliance 100 and intelligence programmed into it by way of the stored program control in memory 105. It is well known that if certain drugs are taken together, a patient can suffer adverse reactions to the drug combinations. A data base of impermissible drug combinations stored within the memory 105 can be scanned using one or more drugs as an index to determine if two or more prescribed drugs should not be taken together. A treatment regimen for one or more drugs to be dispensed by the appliance 100 in combination with others that the patient might be taking himself or by the appliance 100 can be checked against entries in an interactive drug data base to determine if a drug that a patient is taking will adversely affect each other or the patient.

Figure 4A:
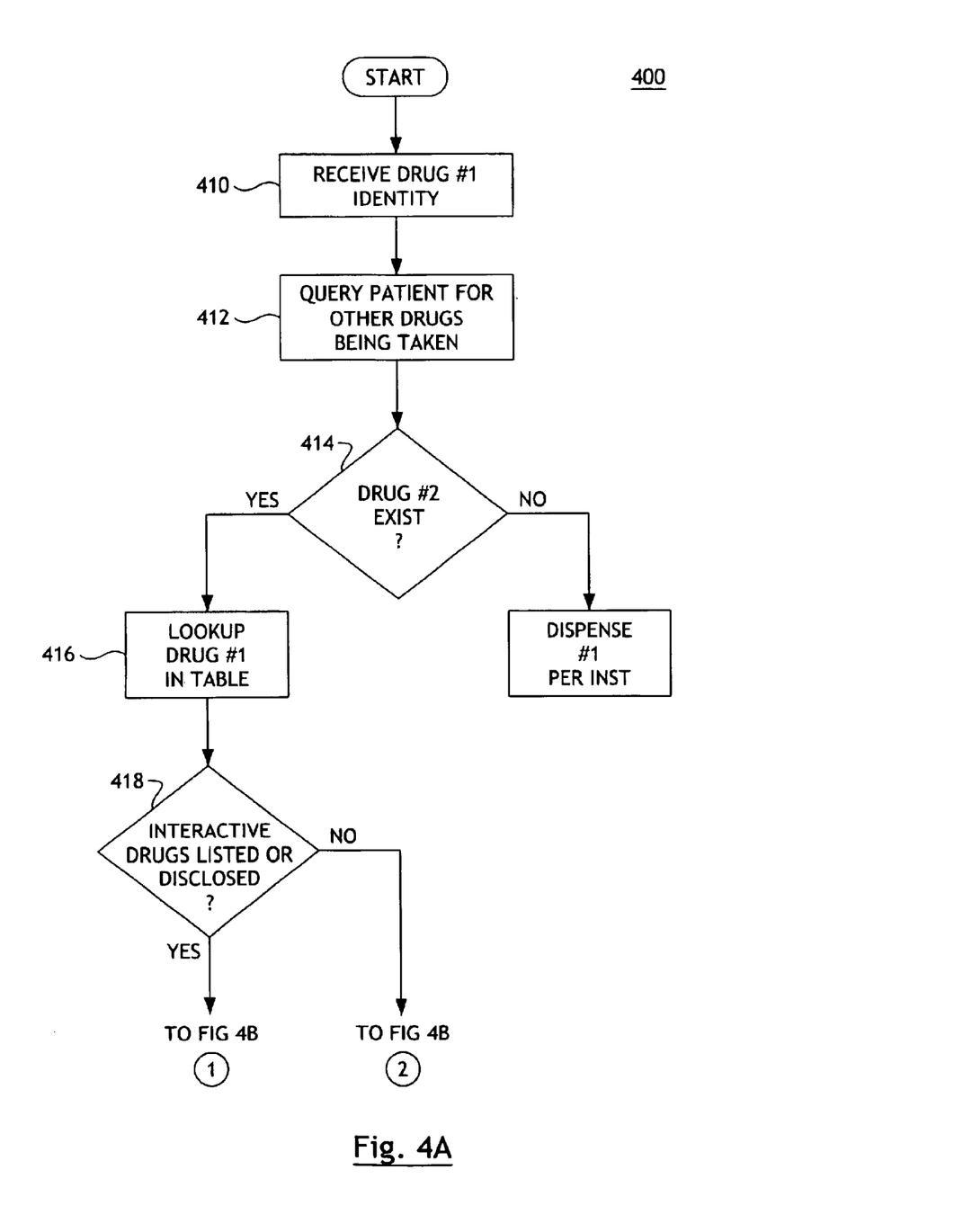
FIG. 4 shows a simplified flow chart depicting a method by which drug interaction can be prevented.
Figure 4B:
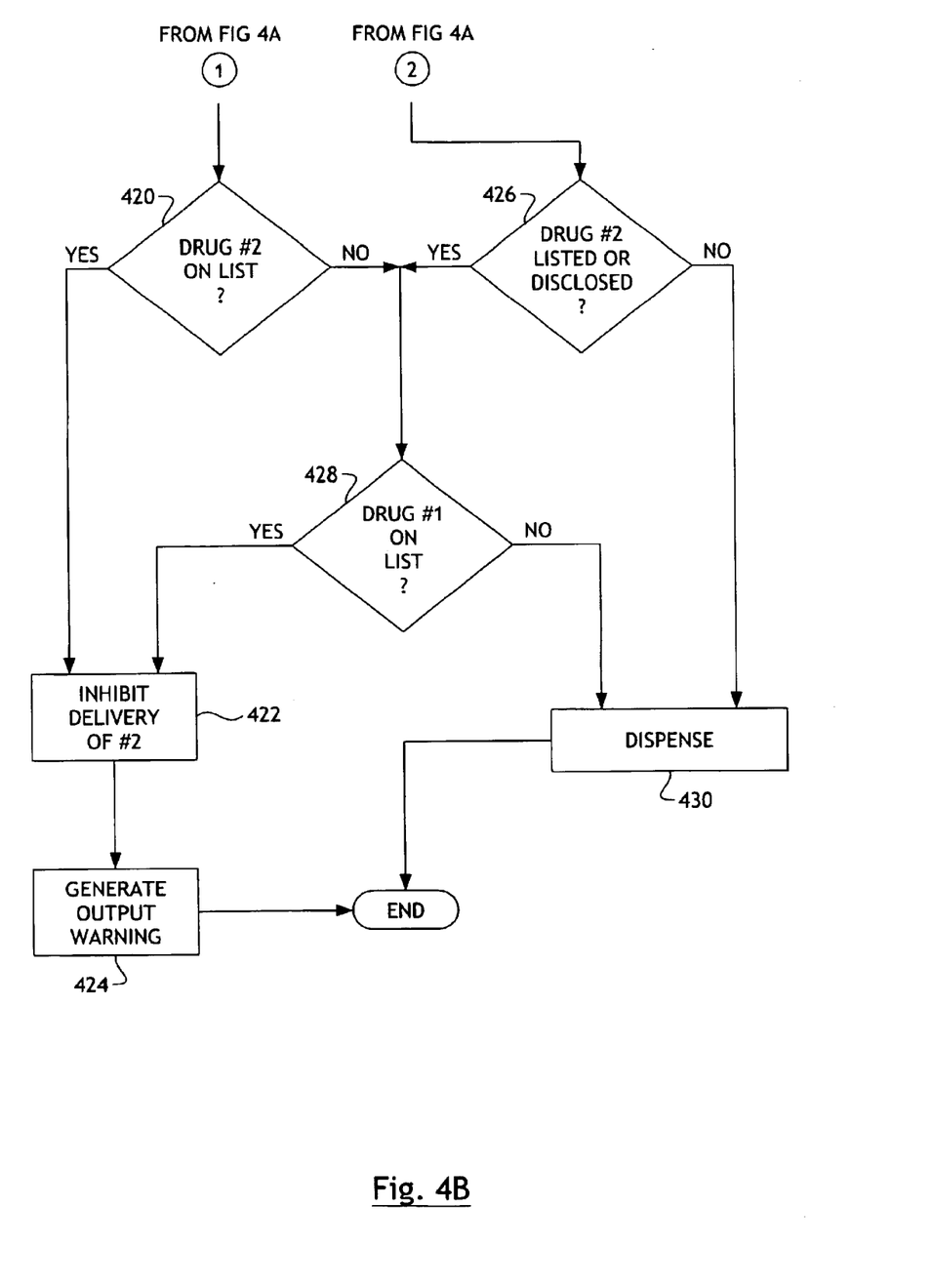

FIGS. 4A and 4B shows a simplified block diagram of the steps of a method 400 by which drug interaction might be avoided. In step 410, a physician or other health care service provider identifies a drug to be dispensed. A drug identity can be provided to the drug delivery appliance 100 by a drug's chemical name or chemical compound as well as its trade name or trademarked name.

A database of the chemical, trade name or trademarked names of drugs that can be dispensed by the appliance can include with each database entry, a data structure (or equivalent) containing the chemical names, trade names or trademark names of drugs that should NOT be dispensed together. When a first drug is known, the drug delivery appliance can query the patient or health care service provider as in step 412 for the names of other drugs that the patient is already taking or which he is supposed to take.

If a second drug is being taken as indicated by an affirmative response in step 414, a database or list of one of the two drugs is searched in step 416 to find one of the two potentially interactive drugs in the database. If one of the potentially interacting drugs is found on the list (A list of data base entries can be quickly and easily searched using a variety of sorting techniques to determine if the drug is included, indicating a potential interaction.) as shown in step 418, indicating that at least one of the drugs is on (or in) the database, in step 420, a database, list or data structure of drugs that should not be combined with the first drug is determined.

In step 422, a determination that the second drug is listed in the database, list or in a data structure of drugs that should not be mixed with the first drug causes the drug delivery appliance to inhibit drug delivery of both drugs in step 422. An output warning (e.g., audible alarm, flashing light, emergency phone call, etc.) in step 424 can be made via the user interface 111 or another output device.

Returning to step 418, a determination that the first of two or more drugs is not on (or in) the drug interaction database causes the system software to determine if the other of the two (or more) drugs is on (or in) the interacting drug data base. Stated alternatively, of two or more drugs that can potentially interact with each other, both are tested for interactive drugs.

In step 426, the presence of drug #2 on (or in) the interacting drug database is tested. If drug #2 is on the list, any associated list or data structure of drugs that drug #2 should not be taken with is queried in step 428. In step 428, if drug #1 is determined to be on (or in) a data base, list or data structure of drugs that should not be taken with drug no. 1, drug delivery is inhibited in step 422. If drug #1 is not on (or in) the database, not listed or not in a data structure of drugs that are not to be taken with drug no. 1, from step 428 the program control passes to step 430 where one or both of the medications can be dispensed.

In performing operations like sorting and listing and comparing using a database of chemical names, trade names or trademarks of drugs, each compound can be assigned a numerical reference identity which corresponds to the drug by its chemical name, trade name or trademark. Searching or sorting numerical entries is computationally faster but more time consuming for the database to be created. By searching for interacting drugs, an enhanced level of patient safety can be realized.

A data transfer network such as the Internet 206, as well as local area networks or even the public switched telephone network can improve patient care even further when treatment regimens stored in the appliance can be modified by a health care service provider in response to real time data forwarded to the health care service provider.

When patient parameters are forwarded to a health care service provider via a data network through the wireless or wireline interfaces (120 and 123 respectively), a programmed treatment regimen can be remotely reprogrammed by data messages sent to the appliance via a network. Web-based data transfers, e-mail or other file transfer protocols enable data, such as dosing parameters, to be adjusted by sending appropriate data messages to the appliance 100 via an electronic communication. By using the nearly instantaneous data transfer capability and nearly ubiquitous availability of the Internet, maintaining a constant supply of health care products can be readily realized.

Those skilled in the medical art will appreciate that patient care might be improved by controlling dosage of drugs according to real-time data. By using readily-available communications capabilities, the method and apparatus disclosed herein could be even more valuable using appropriate wireless communications technologies. By way of example, data on air borne allergen count predictions could be radio broadcast to the 100 appliance via a wireless communications interface 202-5 such as a one or two-way pager, cellular telephone, infrared transmitter or receiver or other wireless device. A wireless communications device enabled with the so-called "Bluetooth" communications protocol for example would enable the system 200 shown in FIG. 2 to be used with other wireless communications devices such that data from the appliance 100 could be transmitted via the wireless interface 202-5 to other equipment (not shown).

What is claimed is:

1. A drug dispensing appliance comprising
   a controller;
   at least one reservoir of pharmaceutical to be dispensed over time to a patient, the reservoir of pharmaceutical configured to contain at least one of tablets, aerosolizable liquids, atomizable liquids, and gases;
   a drug delivery mechanism coupled to, and responsive to the controller and to the reservoir, response to signals from said controller;
   a data network interface coupled to said controller;
   a plurality of patient parameter data input ports coupled to said controller; and
   a plurality of patient parameter sensors, each of which is coupled to at least one patient parameter input port.

2. The drug dispensing appliance of claim 1 further including a wireless communications interface operatively coupled to said controller.

3. The drug dispensing appliance of claim 1 further including an environmental data collections interface operatively coupled to said controller, the environmental data collections interface configured to convey environmental information comprising at least one of ozone, humidity, ultraviolet light intensity, and allergen count.

4. A drug dispensing appliance comprising:
   a controller;
   a reservoir of pharmaceutical to be dispensed over time to a patient, the reservoir of pharmaceutical configured to contain at least one of tablets, aerosolizable liquids, atomizable liquids, and gases;

a drug delivery mechanism coupled to, and responsive to the controller and to the reservoir, to dispense a pharmaceutical to a patient in discrete doses from the reservoir in response to signals from said controller;

a data network interface coupled to said controller;

a plurality of patient parameter data input ports, each operatively coupled to said controller;

a plurality of patient parameter sensors, each of which is coupled to at least one patient parameter input port; and a data network, operatively coupled to said controller over which data signals between said controller and a health care service provider's computer are exchanged.

5. The drug dispensing appliance of claim 4 further including a wireless communications interface coupled to said controller.

6. The drug dispensing appliance of claim 4 further including an environmental data collections interface coupled to said controller.

7. The drug dispensing appliance of claim 1 wherein the drug delivery mechanism comprises at least one inkjet printhead.

8. The drug delivery appliance of claim 7 wherein the drug delivery mechanism is configured to dispense as pharmaceutical at least one of an aerosolized mist or an atomized mist.

9. The drug dispensing appliance of claim 8 wherein the pharmaceutical further comprises at least one consumable supply item.

10. The drug dispensing appliance of claim 1 wherein the pharmaceutical further includes ingestable liquids and wherein the pharmaceutical is dispersed according to a prescription.

11. The drug dispensing appliance of claim 4 wherein the drug delivery mechanism comprises at least one inkjet printhead.

12. The drug dispensing appliance of claim 4 further including an additional reservoir, the additional reservoir configured to dispense at least one consumable supply item.

13. The drug dispensing appliance of claim 12 wherein the consumable supply item comprises at least one of syringes and reagent test strips.

14. A drug dispensing appliance comprising:

a controller;

at least one reservoir of pharmaceutical to be dispensed over time to a patient;

a drug delivery mechanism coupled to, and responsive to the controller and to the reservoir, to dispense a pharmaceutical in discrete doses to a patient from the at least one reservoir in response to signals from said controller according to a treatment regimen, said drug delivery mechanism comprising at least one inkjet printhead for dispensing the pharmaceutical;

a data network interface coupled to said controller;

a plurality of patient parameter data input ports coupled to said controller; and a plurality of patient parameter sensors, each of which is coupled to at least one patient parameter input port;

wherein the pharmaceutical is dispensed according to a prescription and dispensing is governed by the controller.

15. The drug dispensing appliance of claim 14 wherein the pharmaceutical is at least one of a tablet, a gas or a liquid.

16. The drug dispensing appliance of claim 14 wherein the pharmaceutical further comprises at least one consumable supply item and wherein the controller, reservoir, drug delivery mechanism, data network interface, input ports and sensors are configured as a closed-loop system.

17. A drug dispensing appliance comprising:

a controller;

at least one reservoir of pharmaceutical to be dispensed over time to a patient;

a drug delivery mechanism coupled to, and responsive to the controller and to the reservoir, to dispense a pharmaceutical to a patient from the at least one reservoir in response to signals from said controller according to a treatment regimen, said drug delivery mechanism comprising an inkjet printhead for dispensing the pharmaceutical;

a data network interface coupled to said controller;

a plurality of patient parameter data input ports coupled to said controller; and a plurality of patient parameter sensors, each of which is coupled to at least one patient parameter input port.

18. The drug dispensing appliance of claim 17 wherein the controller, reservoir, drug delivery mechanism, data network interface, input ports and sensors are configured as a closed-loop system.

19. A drug dispensing appliance comprising:

a controller;

at least one reservoir of pharmaceutical to be dispensed over time to a patient;

a drug delivery mechanism coupled to, and responsive to the controller and to the reservoir, to dispense a pharmaceutical in discrete doses to a patient from the at least one reservoir in response to signals from said controller according to a treatment regimen;

a data network interface coupled to said controller;

a plurality of patient parameter data input ports coupled to said controller; and a plurality of patient parameter sensors, each of which is coupled to at least one patient parameter input port;

wherein the pharmaceutical is dispensed according to a prescription and dispensing is governed by the controller;

wherein the pharmaceutical further comprises at least one consumable supply item and wherein the controller, reservoir, drug delivery mechanism, data network interface, input ports and sensors are configured as a closed-loop system.

20. The drug dispensing appliance of claim 19 wherein the drug delivery mechanism comprises at least one inkjet printhead.

* * * * *